US012391728B2

(12) United States Patent
Duthe et al.

(10) Patent No.: US 12,391,728 B2
(45) Date of Patent: Aug. 19, 2025

(54) FULL FLOW-THROUGH PROCESS FOR PURIFYING RECOMBINANT PROTEINS

(71) Applicant: SANOFI, Paris (FR)

(72) Inventors: Didier Duthe, Paris (FR); Céline Hemet, Paris (FR); Benoit Mothes, Paris (FR); Jérome Pezzini, Paris (FR)

(73) Assignee: SANOFI, Paris (FR)

( * ) Notice: Subject to any disclaimer, the term of this patent is extended or adjusted under 35 U.S.C. 154(b) by 1074 days.

(21) Appl. No.: 17/040,702

(22) PCT Filed: Mar. 27, 2019

(86) PCT No.: PCT/EP2019/057687
§ 371 (c)(1),
(2) Date: Sep. 23, 2020

(87) PCT Pub. No.: WO2019/185691
PCT Pub. Date: Oct. 3, 2019

(65) Prior Publication Data

US 2021/0009634 A1 Jan. 14, 2021

(30) Foreign Application Priority Data

Mar. 27, 2018 (EP) .................................... 18305338

(51) Int. Cl.

| | |
|---|---|
| ***A61K 39/395*** | (2006.01) |
| ***C07K 1/36*** | (2006.01) |
| ***C07K 16/00*** | (2006.01) |

(52) U.S. Cl.
CPC ................ *C07K 1/36* (2013.01); *C07K 16/00* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 5,891,741 | A | 4/1999 | Olavi et al. |
| 6,602,855 | B2 | 8/2003 | Ludwig et al. |
| 10,131,714 | B2 | 11/2018 | Duthe et al. |
| 10,793,622 | B2 | 10/2020 | Duthe et al. |
| 2002/0009445 | A1 | 1/2002 | Du et al. |
| 2007/0259453 | A1 | 11/2007 | Engstrand et al. |
| 2009/0304710 | A1 | 12/2009 | Park et al. |
| 2011/0065901 | A1 | 3/2011 | Soice et al. |
| 2011/0073548 | A1 | 3/2011 | Williams et al. |
| 2011/0237781 | A1 | 9/2011 | Lebing et al. |
| 2012/0065380 | A1 | 3/2012 | Yoo et al. |
| 2012/0238730 | A1 | 9/2012 | Dong et al. |
| 2012/0322099 | A1 | 12/2012 | Lapen et al. |
| 2013/0245139 | A1* | 9/2013 | Kozlov .................... B01J 39/26 530/413 |
| 2013/0295082 | A1 | 11/2013 | Garidel et al. |
| 2014/0018525 | A1 | 1/2014 | Goklen et al. |
| 2014/0046038 | A1 | 2/2014 | Ishihara |
| 2014/0323698 | A1 | 10/2014 | Duthe et al. |
| 2016/0083454 | A1 | 3/2016 | Duthe et al. |
| 2019/0135942 | A1 | 5/2019 | Duthe et al. |

FOREIGN PATENT DOCUMENTS

| | | | |
|---|---|---|---|
| CN | 1266907 | A | 9/2000 |
| CN | 1504482 | A | 6/2004 |
| CN | 1814775 | A | 8/2006 |
| CN | 101730707 | B | 12/2014 |
| CN | 105358572 | A | 2/2016 |
| EP | 2 360 183 | A1 | 8/2011 |
| EP | 2 415 779 | A1 | 2/2012 |
| JP | 2008-501317 | A | 1/2008 |
| JP | 2008-517906 | A | 5/2008 |
| JP | 2008-533977 | A | 8/2008 |
| JP | 2013-044748 | A | 3/2013 |
| JP | 2015-522019 | A | 8/2015 |
| RU | 2145873 | C1 | 2/2000 |
| RU | 2549710 | C2 | 4/2015 |
| TW | 201313735 | A | 4/2013 |
| WO | WO 1989/003840 | A1 | 5/1989 |
| WO | WO 1995/008574 | A1 | 3/1995 |
| WO | WO 2005/103084 | A2 | 11/2005 |
| WO | WO 2006/043895 | A1 | 4/2006 |
| WO | WO 2006/099875 | A1 | 9/2006 |
| WO | WO 2009/007451 | A1 | 1/2009 |
| WO | WO 2009/099829 | A1 | 8/2009 |
| WO | WO 2009/111347 | A1 | 9/2009 |
| WO | WO 2009/138484 | A2 | 11/2009 |
| WO | WO 2010/071208 | A1 | 6/2010 |

(Continued)

OTHER PUBLICATIONS

European Search Report in related European Patent Application No. EP 17200909, dated Nov. 29, 2017 (5 pages).

(Continued)

*Primary Examiner* — Yunsoo Kim
(74) *Attorney, Agent, or Firm* — MH2 Technology Law Group, LLP

(57) ABSTRACT

The present invention concerns a method for purifying a protein comprising in a continuous mode: one filtration step involving the use of at least one chelating agent, an exchanging step involving the use of at least one diafiltration membrane, and a polishing step involving the use of a combination of membrane adsorbers, wherein two membrane adsorbers of said combination are orthogonal in terms of mechanism of action.

20 Claims, 5 Drawing Sheets

(56) References Cited

FOREIGN PATENT DOCUMENTS

| | | | | |
|---|---|---|---|---|
| WO | WO 2010/082894 A1 | | 7/2010 | |
| WO | WO 2011/049798 A1 | | 4/2011 | |
| WO | WO 2011/090719 A2 | | 7/2011 | |
| WO | WO 2012/135415 A1 | | 10/2012 | |
| WO | WO 2013/028330 A2 | | 2/2013 | |
| WO | WO 2013/075740 A1 | | 5/2013 | |
| WO | WO 2013/075849 A1 | | 5/2013 | |
| WO | WO 2013/096322 A1 | | 6/2013 | |
| WO | WO 2013/096322 A8 | | 6/2013 | |
| WO | WO 2013/096322 A9 | | 6/2013 | |
| WO | WO 2013/138098 A1 | | 9/2013 | |
| WO | WO 2013/189544 A1 | | 12/2013 | |
| WO | WO 2014/004281 A1 | | 1/2014 | |
| WO | 2014180852 A1 | | 11/2014 | |
| WO | WO-2014196780 A1 | * | 12/2014 | ............... C07K 1/18 |

OTHER PUBLICATIONS

International Search Report with Written Opinion corresponding to International Patent Application No. PCT/EP2014/059246, mailed Jul. 17, 2014.
International Search Report with Written Opinion corresponding to International Patent Application No. PCT/EP2012/059528, mailed Jul. 26, 2012.
European Search Report for European Patent Application No. 18305338, dated Sep. 27, 2018, 2 pages.
International Search Report and Written Opinion for PCT International Patent Application No. PCT/EP2019/057687 dated May 31, 2019, 6 pages.
Follman et al., "Factorial Screening of Antibody Purification Processes Using Three Chromatography Steps Without Protein A", Journal of Chromatography A, 2004, vol. 1024, pp. 79-85.
U.S. Appl. No. 14/360,103 2014/0323698 U.S Pat. No. 10,131,714, filed May 22, 2014 Oct. 30, 2014 Nov. 20, 2018, Didier Duthe, Protein Purification Using Bis-Tris Buffer.
U.S. Appl. No. 16/151,963 2019/0135942, filed Oct. 4, 2018 May 9, 2019, Didier Duth, Protein Purification Using Bis-Tris Buffer.
U.S. Appl. No. 14/889,397 2016/0083454 U.S. Pat. No. 10,793,622, filed Nov. 5, 2015 Mar. 24, 2016 Oct. 6, 2020, Didier Duthe, Continuous Multistep Process for Purifying Antibodies.
Boi (2007) "Membrane absorbers as purificaiton tools for monoclonal antibody purificaiton" J. Chromatography B, 848, 19-27.
Bruel et al. (2000) "Rhodopsin Kinase: Two mAbs binding near the carboxyl terminus cause time-dependent inactivation," PNAS, 90(7):3010-3015.
Eriksson et al. (Feb. 2009) "MAb Contaminant Removal with a Multimodal Anion Exchanger," BioProcess International. 7(2):52-56.
European Search Report for European Patent Application No. 17200909.4, dated Nov. 29, 2017.
Follman et al. (2004) "Factorial screening of antibody purification processes using three chromatography steps without protein A," J. Chromatogr. A. 1024:79-85.
GE Healthcare Life Science, Multimodal Chromatography Handbook, 116 pages, retrieved from http://proteins.gelifesciences.com/~/media/protein-purification-ib/documents/handbooks/multidonal_chromatography.pdf?la=en, on Jan. 4, 2017.
GE Healthcare, Capto adhere Instructions 28-9064-05 AA, Multimodel media, 32 pages.
GE Healthcare, Rapid process development for purification of a MAb using AKTA avant 25, 2009, pp. 1-8, retrieved from https://www.gelifesciences.com/gehcls_images/GELS/Related%20Content/Files/1314787424814/litdoc28957347AB_20110831143417.pdf on Jun. 9, 2016.
Gottschalk (2008) "Bioseparation in Antibody manufacturing: the good, the bad and the ugly" Biotechnol. Prog, 24, 496-503.
Gronberg et al., "A tool for increasing the liftime of chromatography resins", mAbs, Mar./Apr. 2011, 3(2): 192-202.
Horio et al.: Eds. (2000) "12.2 Good's buffer," Basic Experimental Methods for Proteins and Enzymes (in Japanese). Revised 2nd Version. pp. 554-555. (a Japanese experimental protocol book in which Table 12-2 "Good's buffers" shows Bis-Tris at the second line, the relevant portion of this document).
International Search Report with Written Opinion for International Patent Application No. PCT/EP2012/059528, mailed Jul. 26, 2012.
International Search Report with Written Opinion for PCT International Patent Application No. PCT/EP2014/059246, mailed Jul. 17, 2014.
Japan Biochemical Society: Eds. (1990) Protein I: Isolation, Purification and Properties. 1st Ed. pp. 324-327.—provided with an English machine translation.
Kallberg et al., "Multimodal chromatography: An efficient tool in downstream processing of proteins", Biotechnol. J., 2012, 7: 1485-1495.
Landric-Burtin et al. (2011) "How to shorten downstream processing for Monoclonal antibodies," Presentation by Sanofi-Aventis, Biologics Center. European Downstream Technology Forum, May 24-25, 2011, Goettingen, Germany. 24 pages.
Liu et al. (2010) "Recovery and purification process development for monoclonal antibody production," mAbs 2(5):480-499.
Mahajan et al., "Improving affinity chromatography resin efficiency using semi-continuous chromatography", Journal of Chromatography A (2012), vol. 122, pp. 154-162.
Pollock et al. (Jan. 25, 2013) "Optimising the design and operation of semi-continuous affinity chromatography for clinical and commercial manufacture," J. Chromatogr. A. 1284:17-27.
Qian et al. (2007) "Conjugating recombinant proteins to Pseudomonas aeruginosa ExoProtein A: A strategy for enhancing immunogenicity of malaria vaccine candidates," Vaccine. 25(20):3923-3933.
Riordan et al., "Design of Salt-Tolerant Membrane Adsorbers for Viral Clearance", Biotechnol Bioeng., 2009, 103: 920-929.
Shamashkin et al., "A tandem laboratory scale protein purification process using protein A affinity and anion exchange chromatograph operated in a weak partitioning mode", Biotechnology and Bioengineering (2013), vol. 110 (10), pp. 2655-2663.
Shukla et al., "Downstream processing of monoclonal antibodies—Application of platform approaches", Journal of Chromatography B, 2007, 8: 28-39.
Topin, Antibody Purification: Tips and Tricks, Supply Discovery Tools, tebubio.com, Sep. 9, 2019, 13 pages.
Verdoliva et al. (2002) "Affinity purification of polyclonal antibodies using a new all-D synthetic peptide ligand: comparison with protein A and protein G," J. Immunol. Methods. 271(1-2):77-88.
Wensel et al., "High-Throughput Screening of Chromatographic Separations: III. Monolonal Antibodies on Ceramic Hydroxyapatite", Biotechnology and Bioengineering, Mar. 19, 2008, 100(5): 839-854.
Yamada et al., 2017, "Purification of Monoclonal Antibodies entirely in flow-through mode", Journal of Chromatography B Analyt Technol Biomed Life Sci., Sep. 1, 2017, 1061-1062: 110-116, ePublished Jul. 3, 2017.
Zhou et al., Purification and Characterization of the Prohormone Convertase PCI(PC3), Journ Biological Chemistry, 1993, 268(8): 5615-5623.

* cited by examiner

FULL FLOW-THROUGH PROCESS FOR PURIFYING RECOMBINANT PROTEINS

RELATED APPLICATIONS

This application is a 35 U.S.C. § 371 filing of International Patent Application No. PCT/EP2019/057687, filed Mar. 27, 2019, which claims priority to European Patent Application No. 18305338.8, filed Mar. 27, 2018, the entire disclosures of which are hereby incorporated herein by reference.

TECHNICAL FIELD

The invention relates to a full flow-through purification process for small and large-scale purification of proteins, specifically monoclonal antibodies.

BACKGROUND

Antibody purification can be one of the most costly aspects of bioproduction. Monoclonal antibodies (mAbs) are generally purified using a three-step, three resin chromatography processes, using at least a specific buffer system at each step. This conventional purification process encompasses a capture step, followed by an intermediate purification step, and concludes with a polishing step, and usually takes 3 to 5 working days (including storages and open phases). In such conventional processes, these three steps are carried out in a sequence of distinct unit operations, which cannot be operated in a continuous mode as adjustment of pH, molarity and protein concentration are necessary between each step. Accordingly, conventional purification processes generally require numerous different buffers as well as numerous storage units between each discontinued step and several systems. These conventional purification processes are thus prone to contaminations, technical failures and human errors. Additionally, since an interruption is needed between each step for concentrating the eluate, adjusting pH and conductivity and storing the eluate before the next step, and since a step cannot start before completion of the previous one, such conventional purification processes are particularly long and expensive.

The high cost of conventional processes is also due to the general use of Protein A matrix as a first step of purification. Indeed, historically, the most selective resin is generally put early in the process, which is the case of Protein A, to remove as many impurities as possible. However, even if the Protein A is the most selective media for monoclonal antibodies purification, there are still contaminants remaining in the process. This step is also the most expensive of the entire process, also because it is used as a first step being contacted with a high amount of contaminants. Additionally, the remaining contaminants are very difficult to remove to be compliant with pharmaceutical specifications.

With increasing cell culture titers and larger cell culture volumes being used for production, downstream processing is viewed as an industry bottleneck. This is particularly relevant to monoclonal antibody production, where the focus has shifted away from batch volume, and towards downstream processing capacity. Furthermore, early preclinical and clinical phase studies require larger amounts of antibodies that can be produced more rapidly. Therefore, a need exists in the industry for a cheaper process, which can be carried out in a continuous mode, for protein purification, in particular for antibody purification, and for both a reduction in the time taken for obtaining batches, in the risks of contaminations, technical failures and human errors and in the process scale-up requirements.

SUMMARY OF INVENTION

The inventors have found a new method for purifying proteins, in particular antibodies, said method comprising only three steps in a continuous full flow-through mode, none of these steps involving Protein A, and advantageously using only one buffer while still allowing obtaining high yields of purified antibodies with an excellent degree of purity. The purified proteins are thus suitable for medical applications. Accordingly, the method may be used to purify proteins for clinical trials and/or for manufacturing a pharmaceutical composition comprising the protein. Additionally, this method does not need any inter-step adjustment and can thus be carried out in a closed system from the harvest of proteins to be purified to the final product.

Briefly, this method comprises only three successive steps, the cheaper technology aiming at removing a big quantity of contaminants being used as the first step, the technologies used for the second and the third steps being more and more selective in order to remove the remaining small amount of contaminants and thus being used in smaller sizes compared to their use in conventional processes.

The method of the invention thus comprises in a continuous mode: one filtration step involving the use of at least one chelating agent, an exchanging step involving the use of at least one diafiltration membrane, and a polishing step involving the use of a combination of membrane adsorbers, wherein two membrane adsorbers of said combination of membrane adsorbers are orthogonal in terms of mechanism of action. The method of the invention is schematized on FIG. 1. These three purification steps are advantageously implemented in this specific order. In addition, it has been found that only one buffer, the buffer used for the exchanging step needs to be used over the whole process. In other words, the equilibration buffer optionally used during the polishing step is advantageously identical to the buffer used for the exchanging step. This buffer advantageously comprises Bis Tris, Tris, Tris-HCl, phosphate and/or citric acid, for example in combination with NaCl, acetic acid and water. More particularly, it is possible to only use one buffer for the entire process, ensuring compatibility between all steps and enabling supply chain manufacturing and quality control savings and reduced storage needs.

The method of the invention further allows abolishing open phases (i.e. steps where the purification system is opened to carry out a manual operation such as preparing a chromatographic column for a new buffer, diluting the sample, or adjusting its pH), thereby reducing the risk of contamination and giving the possibility to work in a less classified environment. Additionally, since the method of the invention advantageously does not involve the use of any column and mainly uses membrane adsorbers, which are disposable and ready to use, there is no need of storage nor re-use validation, no column preparation or packing nor associated controls, no cleaning validation and limited hardware. The process cycle times are thus shortened, the process scale-up requirements are minimized, and it is possible to reduce operation and storage expenses. Therefore, the method of the invention allows both rapid cost effective production of batches and reducing the occupation time of the purification systems. It is thus suitable for scale-up and purification of recombinant proteins from the bench to the industrial scale.

A specific protocol has been set up and implemented for two different antibodies. In this protocol, the filtered protein solution obtained at the end of the first filtration step is directly passed over the at least one diafiltration membrane, i.e. without undergoing any treatment like pH adjustment, buffer exchange or dilution, and the retentate obtained at the end of the exchanging step is also directly passed over the combination of at least two membrane adsorbers, i.e. without undergoing any treatment like pH adjustment, buffer exchange or dilution. This protocol has the advantage of being extremely rapid (a few hours), leads to a high yield (more than 70%), purity compatible with pharmaceutical industry standards and enables reducing both buffers and storage facilities used. Moreover, this process has the advantage of being extremely flexible and cost-saving since it does not involve the use of Protein A matrix, which is generally the most expensive element of conventional processes. In addition, it can be completely automated, run in continuous mode, and it does not comprise any open phase. Moreover, it was successfully carried out for two different antibodies.

The invention thus provides a method for purifying a protein from solution comprising:

(a) a filtration step comprising:
 passing said solution over at least one chelating agent matrix in the flow-through mode,
 recovering a filtered protein solution from the flow-through of said at least one chelating agent matrix;
(b) an exchanging step comprising:
 passing the filtered protein solution obtained at the end of step (a) over at least one diafiltration membrane using only one buffer for the exchange,
 recovering the partly purified protein-containing retentate of said at least one diafiltration membrane;
(c) a polishing step comprising:
 passing the retentate obtained at the end of step (b) over a combination of membrane adsorbers in the flow-through mode, wherein two membrane adsorbers of said combination of membrane adsorbers are orthogonal in terms of mechanisms of action, and said combination of membrane adsorbers has been equilibrated beforehand with an equilibration buffer which is identical to the one buffer used for exchange at step (b),
 recovering purified protein from the flow-through of said combination of membrane adsorbers;

wherein said purifying method does not include a Protein A chromatography step.

The invention also provides a method for purifying a protein from solution comprising:

(a) a filtration step comprising:
 passing said solution over at least one chelating agent matrix in the flow-through mode,
 recovering a filtered protein solution from the flow-through of said at least one chelating agent matrix;
(b) an exchanging step comprising:
 passing the filtered protein solution obtained at the end of step (a) over at least one diafiltration membrane using only one buffer for the exchange, said only one buffer being identical to the equilibration buffer used during the polishing step (c);
 recovering the partly purified protein-containing retentate of said at least one diafiltration membrane;
(c) a polishing step comprising:
 passing the retentate obtained at the end of step (b) over a combination of membrane adsorbers in the flow-through mode, wherein two membrane adsorbers of said combination of membrane adsorbers are orthogonal in terms of mechanisms of action, and said combination of membrane adsorbers has been equilibrated beforehand with the equilibration buffer,
 recovering purified protein from the flow-through of said combination of membrane adsorbers;

wherein said purifying method does not include a Protein A chromatography step.

The invention in particular provides a method for purifying a protein from solution comprising:

(a) a filtration step comprising:
 (i) passing the solution over the at least one chelating agent matrix in the flow-through mode,
 (ii) recovering a filtered protein solution from the flow-through of said at least one chelating agent matrix,
(b) an exchanging step comprising:
 (i) passing the filtered protein solution obtained at the end of step (a) over the at least one diafiltration membrane using only one buffer for the exchange,
 (ii) recovering the partly purified protein-containing retentate of said at least one diafiltration membrane;

and (c) a polishing step comprising:
 (i) passing equilibration buffer over the combination of membrane adsorbers, wherein said equilibration buffer is identical to the one buffer used for exchange at step (b),
 (ii) passing the retentate obtained from step (b) over the combination of membrane adsorbers in the flow-through mode,
 (iii) recovering purified protein from the flow-through of said combination of membrane adsorbers;

wherein said purifying method does not include a Protein A chromatography step.

In one embodiment of the invention, only one buffer is used over the whole purification method. In a particular embodiment, the one buffer comprises Tris, Tris-HCl, Bis Tris, phosphate and/or citric acid. In another embodiment, the one buffer comprises or consists of (i) Bis Tris, Tris or Tris-HCl, (ii) acetic acid, (iii) water and (iv) optionally salt.

In one embodiment, the at least one chelating agent matrix of the filtration step is selected from activated carbons, diatomite earth, free cationic exchange resin, free anionic exchange resin, and free mixed mode resin. In a particular embodiment, the at least one chelating agent matrix is a combination of two different chelating agent matrices. In a more particular embodiment, the combination of two different chelating agent matrices is a combination of activated carbons and free anionic exchange resin. In another particular embodiment, the at least one chelating agent matrix is a combination of more than two different chelating agent matrices, i.e. three, four, five or more than five.

In one embodiment, the at least one diafiltration membrane of the exchanging step is a single-path tangential flow filtration (SPTFF) module or a tangential flow filtration (TFF) module. In a particular embodiment, the at least one diafiltration membrane of the exchanging step is in the form of a cassette, a hollow fiber or a spiral wound. In a particular embodiment, the filtered protein solution is concentrated during the exchanging step.

In one embodiment, the combination of membrane adsorbers of the polishing step is a combination of two membrane adsorbers or a combination of at least two membrane adsorbers, for example three, four or at least four membrane adsorbers.

In one embodiment, the membrane adsorbers of the combination of membrane adsorbers are selected from the group consisting of cationic-exchange membrane adsorber, anionic-exchange membrane adsorber, multi-modal membrane adsorber, hydrophobic interaction membrane adsorber and their combinations. In a particular embodiment, the combination of membrane adsorbers of the polishing step is a combination of a cationic-exchange membrane adsorber and an anionic-exchange membrane adsorber.

In one embodiment, the combination of membrane adsorbers of the polishing step is a combination of at least two membrane adsorbers selected from the group consisting of cationic-exchange membrane adsorbers, anionic-exchange membrane adsorbers, multi-modal membrane adsorbers and hydrophobic interaction membrane adsorbers.

In one embodiment of the invention, the method further comprises a nanofiltration step after step (c) and optionally a final ultrafiltration and/or diafiltration step after the nanofiltration step. In another embodiment of the invention, the method further comprises a low pH inactivation step after step (c), after the nanofiltration step and/or after the final ultrafiltration and/or diafiltration step. In one embodiment of the invention, the method comprises, before step (a), a step of cell culture in a liquid culture medium, preferably in a bioreactor, to provide a liquid culture medium containing the protein. The cultured cells may be mammalian, bacterial or yeast cells. In a preferred embodiment, the cultured cells may be mammalian cell lines (e.g., Vero cells, CHO cells, 3T3 cells, COS cells, HEK293 cells, etc. including the different subtypes of these cell lines) as well as primary or established mammalian cell cultures (e.g., produced from lymphoblasts, fibroblasts, embryonic cells, epithelial cells, nervous cells, adipocytes, etc.).

In one embodiment of the invention, the protein being purified is an antibody. In another embodiment, the antibody is a monoclonal antibody.

The invention therefore also provides an integrated process for the generation of a purified protein from a liquid culture medium.

In certain embodiments of the invention, the one buffer comprises 5 to 40 mM (in particular 20 mM) Bis Tris, 15 to 150 mM (in particular 75 mM) NaCl, adjusted to a pH comprised between 6 and 9 (in particular 7.5) with acetic acid.

In certain embodiments of the invention, the one buffer comprises 5 to 40 mM (in particular 20 mM) Tris or Tris-HCl, 15 to 150 mM (in particular 75 mM) NaCl, adjusted to a pH comprised between 6 and 9 (in particular 7.5) with acetic acid.

In certain embodiments of the invention, the one buffer comprises 5 to 40 mM (in particular 20 mM) Tris or Tris-HCl, 15 to 150 mM (in particular 75 mM) NaCl, adjusted to a pH comprised between 6 and 9 (in particular 7.5) with citric acid.

In certain embodiments of the invention, the one buffer comprises 15 to 150 mM (in particular 75 mM) NaCl, adjusted to a pH comprised between 6 and 9 (in particular 7.5) with $Na_2HPO_4/NaH_2PO_4$ (preferably from 10 mM/90 mM $Na_2HPO_4/NaH_2PO_4$ to 90 mM/10 mM $Na_2HPO_4/NaH_2PO_4$).

The invention provides a kit comprising at least one chelating agent matrix, at least one diafiltration membrane and a combination of membrane adsorbers, wherein two membrane adsorbers of said combination of membrane adsorbers are orthogonal in terms of mechanisms of action; and one buffer comprising Tris, Tris-HCl, Bis Tris, phosphate and/or citric acid, in particular comprising or consisting of (i) Bis Tris, Tris or Tris-HCl, (ii) acetic acid, (iii) water, and (iv) optionally NaCl. In some embodiments, the kit is used for purifying a protein from solution using a method of the invention.

The invention also provides a kit comprising at least one chelating agent matrix, at least one diafiltration membrane and a combination of membrane adsorbers, wherein two membrane adsorbers of said combination of membrane adsorbers are orthogonal in terms of mechanisms of action; and instructions for preparing one buffer comprising Tris, Tris-HCl, Bis Tris, phosphate and/or citric acid, in particular comprising or consisting of (i) Bis Tris, Tris or Tris-HCl, (ii) acetic acid, (iii) water, and (iv) optionally NaCl. In some embodiments, the kit is used for purifying a protein from solution using a method of the invention.

Also provided herein are isolated proteins, pharmaceutical agents and pharmaceutical compositions obtained by any of the methods described herein.

These and other features and advantages of the disclosed purification method will be more fully understood from the following detailed description taken together with the accompanying claims. It is noted that the scope of the claims is defined by the recitations therein and not by the specific discussion of features and advantages set forth in the description.

In the context of the invention, the terms "comprising", "having", "including" and "containing" are to be construed as open-ended terms (i.e., meaning "including, but not limited to,") unless otherwise noted. Additionally, the term "comprising" encompasses "consisting" (e.g., a composition "comprising" X may consist exclusively of X or may include something additional, e.g., X+Y).

DETAILED DESCRIPTION OF ASPECTS AND EMBODIMENTS

Willing to simplify protein purification processes and make them cheaper, the inventors have developed a new purification process which is continuous, full flow-through and does not include a Protein A chromatography step.

The invention pertains to a method for purifying a protein from solution comprising:

(a) a filtration step comprising:
  - passing said solution over at least one chelating agent matrix in the flow-through mode,
  - recovering a filtered protein solution from the flow-through of said at least one chelating agent matrix;

(b) an exchanging step comprising:
  - passing the filtered protein solution obtained at the end of step (a) over at least one diafiltration membrane using only one buffer for the exchange,
  - recovering the partly purified protein-containing retentate of said at least one diafiltration membrane;

(c) a polishing step comprising:
  - passing the retentate obtained at the end of step (b) over a combination of membrane adsorbers in the flow-through mode, wherein two membrane adsorbers of said combination of membrane adsorbers are orthogonal in terms of mechanisms of action, and said combination of membrane adsorbers has been equilibrated beforehand with an equilibration buffer which is identical to the one buffer used for exchange at step (b),
  - recovering purified protein from the flow-through of said combination of membrane adsorbers;

wherein said purifying method does not include a Protein A chromatography step.

In the exchanging step (b), the expression "passing the filtered protein solution obtained at the end of step (a) over at least one diafiltration membrane using only one buffer for the exchange" means that said filtered protein solution and the one buffer are passed over the at least one diafiltration membrane.

In a particular embodiment, the method of the invention comprises:

(a) a filtration step comprising:
 (i) passing the solution over the at least one chelating agent matrix in the flow-through mode,
 (ii) recovering a filtered protein solution from the flow-through of said at least one chelating agent matrix,
(b) an exchanging step comprising:
 (i) passing the filtered protein solution obtained from step (a) over the at least one diafiltration membrane using only one buffer,
 (ii) recovering the partly purified protein-containing retentate of said at least one diafiltration membrane;
and
(c) a polishing step comprising:
 (i) passing equilibration buffer over the combination of membrane adsorbers, wherein said equilibration buffer is identical to the one buffer used for exchange at step (b),
 (ii) passing the retentate obtained from step (b) over the combination of membrane adsorbers in the flow-through mode,
 (iii) recovering purified protein from the flow-through of said combination of membrane adsorbers, wherein said purifying method does not include a Protein A chromatography step.

As indicated above, the above method of the invention only comprises three steps, none of them being a Protein A chromatography step. Even though the method according to the invention only comprises three steps and no Protein A chromatography step, it allows obtaining purified proteins that are suitable for pharmaceutical purposes and in particular for administration to human beings.

In addition to the absence of human handling in the purification process (and consequent reduction in the overall time required to complete the purification process), the disclosed method reduces the amount of buffers used for purification and the absence of a Protein A chromatography step reduces costs. The disclosed purification method also simplifies mAb purification, improves the overall yield, and reduces raw materials, storage facilities, cost of goods and process time, in addition to allowing for the purification of a variety of mAbs.

In contrast with conventional protein purification methods, as stated above, the method disclosed herein uses one unique buffer, this unique buffer being used for the exchanging step and to equilibrate the membrane adsorbers in the polishing step.

As used herein, "buffers according to the invention" refer to buffers comprising Bis Tris, Tris, Tris-HCl, phosphate and/or citric acid. Bis Tris, Tris or Tris-HCl are compounds well known to the skilled in the art:

- the IUPAC name of which is 2-[bis(2-hydroxyethyl) amino]-2-(hydroxymethyl)propane-1,3-diol, and the CAS Number of which is 6976-37-0 for Bis Tris,
- 2-amino-2-(hydroxymethyl)propane-1,3-diol and CAS Number 77-86-1 for Tris, and
- 2-amino-2-(hydroxymethyl)propane-1,3-diol Hydrochloride and CAS Number 1185-53-1 for Tris-HCl.

Such buffer according to the invention may correspond to an exchanging buffer, and to an equilibration buffer.

More specifically, such buffer according to the invention may comprise or consist of varying concentrations of the same chemicals (one of them being Bis Tris, Tris, Tris-HCl, phosphate and/or citric acid). In a particular embodiment, the buffer comprises Bis Tris, Tris, Tris-HCl, phosphate and/or citric acid. In a specific embodiment, the buffer comprises or consists of (i) Bis Tris, Tris, or Tris-HCl, (ii) acetic acid and (iii) water. In a more specific embodiment, the buffer comprises or consists of (i) Bis Tris, Tris or Tris-HCl, (ii) acetic acid, (iii) NaCl and (iv) water. In other terms, such buffer comprises or consists of varying concentrations of (i) Bis Tris, Tris or Tris-HCl, (ii) acetic acid, (iii) NaCl and (iv) water.

The exchanging buffer may for example comprise or consist of 5 to 40 mM (e.g. 20 mM) Bis Tris and 15 to 150 mM (e.g. 75 mM) NaCl, adjusted to a pH comprised between 6 and 9 (e.g. 7.5) with acetic acid.

The exchanging buffer may alternatively comprise or consist of 5 to 40 mM (in particular 20 mM) Tris or Tris-HCl, 15 to 150 mM (in particular 75 mM) NaCl, adjusted to a pH comprised between 6 and 9 (in particular 7.5) with acetic acid.

The exchanging buffer may alternatively comprise or consist of 5 to 40 mM (in particular 20 mM) Tris or Tris-HCl, 15 to 150 mM (in particular 75 mM) NaCl, adjusted to a pH comprised between 6 and 9 (in particular 7.5) with citric acid.

The exchanging buffer may alternatively comprise or consist of 15 to 150 mM (in particular 75 mM) NaCl, adjusted to a pH comprised between 6 and 9 (in particular 7.5) with $Na_2HPO_4/NaH_2PO_4$ (preferably from 10 mM/90 mM $Na_2HPO_4/NaH_2PO_4$ to 90 mM/10 mM $Na_2HPO_4/NaH_2PO_4$).

Such exchanging buffers are notably suitable for use with an exchanging step, in particular with TFF cassettes, but also suitable for equilibration of membrane adsorbers, in particular equilibration of a combination of cationic-exchange membrane adsorber and anionic-exchange membrane adsorber.

Advantages of the above buffer formulations include the capability for a mAb product to pass through the three steps of the method, in particular the exchanging step and the polishing step, with larger compatibility, while minimizing undesired interactions, limiting pH and conductivity drops, and promoting increased yield versus traditional purification methods. The use of such buffer formulation enables implementing the method without any intermediate storage between the three steps (a), (b) and (c).

Accordingly, in a particular embodiment, the method does not comprise any intermediate storage between the three steps (a), (b) and (c).

A sanitization buffer may optionally be used when the membrane adsorbers of the polishing step are re-used. Such a sanitization buffer may comprise or consist of at least NaOH, more preferably 0.05 N to 1 N (e.g. 0.5 N) NaOH.

The terms "polypeptide" or "protein" as used herein refer to:

1) molecules having the sequence of native proteins, that is a) proteins produced by naturally-occurring and specifically non-recombinant cells, or b) genetically-engineered or recombinant cells, or
2) molecules differing from the sequence of native proteins by deletions from, additions to, and/or substitutions of one or more amino acids and/or by at least one post-translational modification (e.g. glycosylation).

The molecules mentioned in the paragraph 1) above may be called native proteins.

The molecules mentioned in the paragraph 2) above are non-natural proteins.

In certain aspects, the protein to be purified is an antibody.

The term "antibody" as used herein refers to an intact antibody, or a binding fragment thereof that competes with the intact antibody for specific binding. Binding fragments include, but are not limited to, F(ab), F(ab'), $F(ab')_2$, Fv, single-domain antibodies such as VHH antibodies (nanobodies) and single-chain antibodies. The term "heavy chain" includes any immunoglobulin polypeptide having sufficient variable region sequence to confer specificity for an antigen.

The term "heavy chain" as used herein encompasses a full-length heavy chain and fragments thereof. A full-length heavy chain includes a variable region domain, VH, and three constant region domains, CH1, CH2, and CH3. The VH domain is at the amino-terminus of the polypeptide, and the CH3 domain is at the carboxyl-terminus.

The term "light chain" as used herein encompasses a full-length light chain and fragments thereof. A full-length light chain includes a variable region domain, VL, and a constant region domain, CL. Like the heavy chain, the variable region domain of the light chain is at the amino-terminus of the polypeptide. The term "light chain" as used herein includes any immunoglobulin polypeptide having sufficient variable region sequence to confer specificity for an antigen.

Naturally occurring antibody structural units typically comprise a tetramer. Each such tetramer typically is composed of two identical pairs of polypeptide chains, each pair having one full-length light chain (typically having a molecular weight of about 25 kDa) and one full-length heavy chain (typically having a molecular weight of about 50-70 kDa). The amino-terminal portion of each light and heavy chain typically includes a variable region of about 100 to 110 or more amino acids that typically is responsible for antigen recognition. The carboxy-terminal portion of each chain typically defines a constant region responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids.

The variable regions of each light/heavy chain pair typically form the antigen-binding site. The variable regions typically exhibit the same general structure of relatively conserved framework regions (FR) joined by three hypervariable regions, also called complementarity determining regions or CDRs. The CDRs from the two chains of each pair typically are aligned by the framework regions, which may enable binding to a specific epitope. From N-terminal to C-terminal, both light and heavy chain variable regions typically comprise the domains FR1, CDR1, FR2, CDR2, FR3, CDR3, and FR4. The assignment of amino acids to each domain is typically in accordance with the definitions of Kabat et al., 1991, Sequences of Proteins of Immunological Interest, 5th ed., U.S. Department of Health and Human Services, NIH Publication No. 91-3242. A bispecific or bifunctional antibody typically is an artificial hybrid antibody having two different heavy chain/light chain pairs and two different binding sites.

A F(ab) fragment is comprised of one light chain and the CH1 and variable regions of one heavy chain. The heavy chain of a F(ab) molecule cannot form a disulfide bond with another heavy chain molecule. A F(ab') fragment contains one light chain and one heavy chain that contains more of the constant region, between the CH1 and CH2 domains, such that an interchain disulfide bond can be formed between two heavy chains to form an $F(ab')_2$ molecule. The Fv region comprises the variable regions from both the heavy and light chains, but lacks the constant regions. Single-chain antibodies are Fv molecules in which the heavy and light chain variable regions have been connected by a flexible linker to form a single polypeptide chain, which forms an antigen-binding region. A bivalent antibody other than a "multispecific" or "multifunctional" antibody, in certain embodiments, is understood to comprise binding sites having identical antigenic specificity.

Monoclonal antibodies (mAbs) that can be purified by the disclosed method can be produced by a variety of techniques, including conventional monoclonal antibody methodology, e.g., the standard somatic cell hybridization technique well known in the art. Although somatic cell hybridization procedures are preferred, in principle, other techniques for producing monoclonal antibodies can be employed, e.g., viral or oncogenic transformation of B-lymphocytes. The monoclonal antibody may for instance correspond to a murine, a chimeric, a humanized or a fully human antibody.

Non-limiting examples of antibodies that may be purified by the method of the invention also comprise: panitumumab, omalizumab, abagovomab, abciximab, actoxumab, adalimumab, adecatumumab, afelimomab, afutuzumab, alacizumab, alemtuzumab, alirocumab, altumomab, amatuximab, anatumomab, apolizumab, atinumab, tocilizumab, basilizimab, bectumomab, belimumab, bevacizumab, biciromab, canakinumab, cetuximab, daclizumab, densumab, eculizumab, edrecolomab, efalizumab, efungumab, ertumaxomab, etaracizumab, etanercept, golimumab, infliximab, natalizumab, palivizumab, panitumumab, pertuzumab, ranibizumab, rituximab, tocilizumab, trastuzumab, dupilumab, sarilumab or fresolimumab.

In certain aspects, the protein to be purified is an enzyme.

Non-limiting examples of enzymes that may be purified by the method of the invention comprise acid α-glucosidase, α-L-iduronidase, iduronate sulfatase, heparan N-sulfatase, galactose-6-sulfatase, acid β-galactosidase, δ-glucoronidase, N-acetylglucosamine-1-phosphotransferase, α-N-acetylgalactosaminidase (α-galactosidase B), acid lipase, lysosomal acid ceramidase, acid sphingomyelinase, 6-glucosidase, galactosylceramidase, α-galactosidase A, acid β-galactosidase, β-galactosidase, neuraminidase, hexosaminidase A or hexosaminidase B.

Other non-limiting examples of proteins that may be purified by the method of the invention comprise human erythropoietin, tumor necrosis factor (e.g. TNF-α, TNF-β or TNF-K), interferon alpha or interferon beta.

The solution containing the protein to be purified may be a culture medium, preferably a clarified culture medium. The solution containing the protein to be purified is for example a culture medium obtained in a perfusion bioreactor or fed-batch bioreactor.

Examples of perfusion bioreactors or fed-batch bioreactors are disclosed in U.S. patent applications US 2014/255994, US 2015/232505, US 2015/183821 and US 2017/

218012 and international application WO2014/137903 (herein incorporated by reference in its entirety).

The term “clarified culture medium” means a liquid culture medium obtained from a mammalian, bacterial or yeast cell culture that is substantially free (e.g., at least 80%, 85%, 90%, 92%, 94%, 96%, 98%, or 99% free) of mammalian, bacteria or yeast cells.

In a particular embodiment, the first filtration step of the method of the invention may be integrated in a clarification step used to obtain a clarified culture medium during the cell culture recovery, said filtration step thereby becoming part of the clarification step.

The phrase “recovering the protein” as used herein refers to collecting a protein after using the disclosed purification method.

In the context of the invention, the expression “chelating agent” refers to any kind of particulate sorbent media or immobilized ligand, such as activated carbon, diatomite earth, bead resin, which, in a purification process, acts as the absorbent to separate the contaminants molecules present in the mixture from the target molecule to be purified. The expression “chelating agent matrix” does not include Protein A matrix.

In certain embodiments of the method of the invention, the at least one chelating agent matrix is a particulate sorbent media.

The at least one chelating agent matrix can be in the form of columns, filters or added as powder into the product to be purified. In a particular embodiment, the at least one chelating agent matrix used in the context of the invention is added as powder into the product to be purified.

In particular embodiments of the disclosed method, the at least one chelating agent matrix is an activated carbon filter. In other particular embodiments of the disclosed method, the at least one chelating agent is a resin.

The at least one chelating agent matrix, in particular the activated carbon filter or the resin media, interacts with the contaminants, resulting in high efficiency of removal of impurities. Another advantage of using a chelating agent matrix, in particular of using activated carbon or resin, is the low affinity for monoclonal antibodies.

In particular embodiments of the present invention, the at least one chelating agent matrix of the filtration step is selected from the group consisting of activated carbons, diatomite earth, free cationic exchange resin, free anionic exchange resin, and free mixed mode resin. In a particular embodiment, the at least one chelating agent matrix is a combination of two different chelating agent matrices. In a more particular embodiment, the combination of two different chelating agent matrices is a combination of activated carbons, in particular activated carbon filters, and free anionic exchange resin.

In a particular embodiment of the disclosed method, the activated carbon filter is Zeta Plus 35SP (commercialized by 3M), Zeta Plus 53SP (commercialized by 3M), Millistak CR40 (commercialized by Millipore) or Zeta Plus 55SP grade (commercialized by 3M).

In another particular embodiment of the disclosed method, the free anionic exchange resin is the NH2-750F (commercialized by Tosoh) or Emphaze AEX (commercialized by 3M). The characteristics of the resin NH2-750F are summarized below.

| | |
|---|---|
| Pore size (mean) | >100 nm |
| Particle size (mean) | 45 μm (F-grade) |
| Pressure rating | 0.3 Mpa |
| pH stability | 2-13 |
| Shelf life | 10 years (estimated) |

In the context of the invention, the expression “diafiltration” refers to a technique that uses ultrafiltration membranes to completely remove, replace, or lower the concentration of salts or solvents from solutions.

As used herein, “ultrafiltration” or “UF” refers to a filtration technique using a semi-permeable membrane to physically and selectively remove particles and/or ions from a solution based on particle size and size of the pores in the UF membrane.

In one embodiment, the at least one diafiltration membrane of the exchanging step is a single-path tangential flow filtration (SPTFF) module or a tangential flow filtration (TFF) module. In a particular embodiment, the at least one diafiltration membrane of the exchanging step is in the form of a cassette, a hollow fiber or a spiral wound.

In a particular embodiment of the disclosed method, the at least one diafiltration membrane of the exchange step is a Ready To Process hollow fiber cartridge 30 kDa (commercialized by GE).

In a particular embodiment of the disclosed method, the at least one diafiltration membrane of the exchange step is a Cadence Inline Diafiltration (commercialized by Pall).

In one embodiment, the at least one diafiltration membrane of the exchange step is preceded or followed by a Cadence Inline Concentrator (Commercialized by Pall).

In another particular embodiment of the disclosed method, the at least one diafiltration membrane of the exchange step is a Pellicon cassette (commercialized by Millipore) or Sartocon cassette (commercialized by Sartorius).

The exchanging step advantageously allows both purifying and concentrating the filtered protein solution. By the expression “concentrating the filtered protein solution”, it is herein meant that the concentration of the protein in the partly purified retentate is increased by comparison to its concentration in the filtered protein solution.

In the context of the invention, a “membrane adsorber” refers to a flat sheet of polymer, in particular acrylic polymer, or a fiber or a non-woven media, bearing functional groups such as affinity groups and ionic exchange groups. One of the differences between resin and membrane is the flow distribution: by diffusion for resin and by convection in membranes.

The combination of membrane adsorbers used in the polishing step, involves the use of at least two kinds of membrane adsorbers which are orthogonal in terms of mechanisms of action.

In the context of the invention, the expression “membrane absorbers which are orthogonal in terms of mechanisms of action” means that the membrane adsorbers used have opposite or distinct mechanisms of action, such a cation-exchange and anion-exchange interactions, multi-modal and anion-exchange interactions, cation-exchange and hydrophobic interactions, or anion-exchange and hydrophobic interactions and act as a sole integrated step, i.e. where they are processed together like if it was a single filtration step.

Indeed, the inventors shown that the use of such a combination of membrane adsorbers enables catching impurities while minimizing the adsorption of the product of interest.

In a preferred embodiment wherein more than two membrane adsorbers are used within the combination of membrane adsorbers of the polishing step, i.e. at least one additional membrane adsorber for a total of three, four or more than four membrane adsorbers, said at least one additional membrane adsorber is a membrane having a different mechanism of action compared to the two membrane adsorbers which are orthogonal in terms of mechanisms of action; this total of more than two membrane adsorbers still being considered as a sole integrated single step.

As a non-limiting example, said at least one additional membrane adsorber has hydrophobic interactions or multimodal interactions if the two membrane adsorbers which are orthogonal in terms of mechanisms of action have cation-exchange and anion-exchange interactions, respectively.

In the context of the invention, the membrane adsorbers are in particular combined as a sole integrated step. The numbers of steps and buffers is therefore drastically reduced. Adjustments and manipulations are also removed hence simplifying the global process. In particular, there is no elution, adjustment or storage steps between one membrane adsorber of the combination of membrane adsorbers and the other(s) membrane adsorber(s) of such combination of membrane adsorbers.

In particular embodiments, the specific combination of membrane adsorbers of the polishing step and the conditions of operation (in particular pH, conductivity and/or buffer) are determined according to the physicochemical properties of the protein to be purified (for example, pl, molecular weight, . . . ).

As will be understood by the skilled person, the optimal conditions of the polishing step should allow obtaining the maximum yield of the protein of interest, i.e. should allow the lowest interaction of the protein of interest with the combination of membrane adsorbers, while allowing the maximum contaminant removal, i.e. while allowing the highest interaction of the contaminants with the combination of membrane adsorbers without any adjustment or elution step between the membrane adsorbers of the combination of membrane adsorbers.

An example of determination of an optimal combination of two membrane adsorbers for the polishing step is exemplified on FIG. 3. In this example, the best purification performances are obtained using a combination of Sartobind S and Sartobind STIC membrane adsorbers, with higher contaminants clearance (lower HCP and HMW) while maximizing antibody yield. The impact of the loading capacity on Yield and contaminant removal is also shown in this Figure.

In the context of the invention, in order to determine these optimal conditions, the membrane adsorbers of the combination of membrane adsorbers should be regarded as a single entity or sole integrated step, i.e. where they are processed together like if it was a single filtration step. For example, in the case of two membrane adsorbers, whereas the conventional way of determining optimal conditions when using two membrane adsorbers involves the determination of the best conditions on the first membrane adsorber, then the determination of the best conditions on the second membrane adsorber and then adjusting the product (such as pH adjustment, conductivity adjustment or buffer adjustment) in between both best conditions, in the context of the invention, the two membrane adsorbers are considered as only one and a compromise should be determined on the separation behavior of the two membrane adsorbers, still enabling obtaining a good purification.

Typically, when determining the optimized buffer to be used for the purification of a given protein, the exchanging step can be performed with a neutral buffer and the pH and conductivity of the solution comprising the retentate can be adjusted manually in order to determine the optimal conditions of purification during the polishing step. When the optimal conditions are determined, the process can be performed again using the appropriate buffer for the exchanging step, which will correspond to the equilibration buffer used for the polishing step.

An example of determination of optimal buffers (such as conductivity or pH of the buffer) according to the combination of two membrane adsorbers used for the polishing step and the pl of the protein of interest is exemplified on FIG. 4. In this example, the conditions of pH and conductivity enabling obtaining an advantageous purification (corresponding to an HCP level comprising between 50 and 500 ng/ml) correspond to the black areas of each plot.

In the context of the invention, the one buffer used for equilibration of the at least two membrane adsorbers is the same as the buffer used for the exchanging step. It allows a direct flow-through of the protein to be purified to maximize the yield while retaining most of the contaminants.

In particular embodiments, the polishing step is optimized by the variation of pH and conductivity of the buffer used to condition the protein during the exchanging step.

In particular embodiments, the polishing step comprises the use of a cationic-exchange membrane adsorber matrix combined with an anionic-exchange membrane adsorber matrix. In other embodiments, the polishing step comprises the use of a multi-modal (mixed-mode) membrane adsorber matrix combined with an anionic-exchange membrane adsorber matrix.

The combination of membrane adsorber matrices, in particular the combination of the cationic-exchange membrane adsorber and of the anionic-exchange membrane adsorber, function via interaction between the membrane adsorber and the contaminants, resulting in high efficiency removal of impurities. The interactions with contaminants are due to several mechanisms: ionic, hydrophobic, van der Walls and hydrogen bond interactions.

In particular embodiments, the cationic-exchange membrane adsorber is a Sartobind S membrane adsorber (Sartorius), an HD-C membrane adsorber (Natrix). In specific embodiments, the cationic-exchange membrane adsorber is a Sartobind S membrane adsorber (Sartorius). In particular embodiments, the anionic-exchange membrane adsorber is a Sartobind STIC membrane adsorber (Sartorius), a Sartobind Q membrane adsorber (Sartorius), or an HD-Q membrane adsorber (Natrix). In specific embodiments, the anionic-exchange membrane adsorber is a Sartobind STIC membrane adsorber (Sartorius) or a Sartobind Q membrane adsorber (Sartorius). In other embodiments, the multi-modal membrane adsorber is a HD-Sb membrane adsorber (Natrix). In other embodiments, the hydrophobic interaction membrane adsorber is a Sartobind Phenyl membrane adsorber (Sartorius).

In a particular embodiment, the combination of membrane adsorbers is a combination of Sartobind S membrane adsorber (Sartorius) and of Sartobind STIC membrane adsorber (Sartorius).

The main advantage of using membrane adsorbers rather than columns in the polishing step of the method of the invention are summarized below:

at comparable scale, membrane adsorbers can be used at a 10 fold higher flow rate than a column, thereby drastically reducing the duration of the process. For example, a 5 mL-column packed with resin will be used at a flow rate of 1 ml/min, whereas a corresponding 5 mL-membrane adsorber will be used at a minimum flow rate of 10 ml/min. Accordingly, when a classical process using two chromatographic steps for polishing, is performed in 2 h 30 using two columns packed with resin, it can be completed in less than 15 min using membrane adsorbers.

even if they are reusable, membrane adsorbers are disposable devices, which can thus be discarded after a batch and do not need to be stored over a long term. It is therefore not necessary to test them to ensure long-term stability.

using membrane adsorbers is cheaper by avoiding column cost, column packing and column storage.

In a particular embodiment, when the combination of membrane adsorbers is a combination of Sartobind S membrane adsorber (Sartorius) and of Startobind STIC membrane adsorber (Sartorius), the one buffer has a pH and a conductivity in the ranges disclosed on the black areas of the upper panels of FIG. 4.

In another particular embodiment, when the combination of membrane adsorbers is a combination of Sartobind S membrane adsorber (Sartorius) and of Startobind Q membrane adsorber (Sartorius), the one buffer has a pH and a conductivity in the ranges disclosed on the black areas of the lower panels of FIG. 4.

The method of purification according to the invention is a full flow-through purification method.

By "full flow-through purification method" is meant herein that the different purification steps of the method all imply the binding of impurities only while leaving the protein of interest go through the purification steps.

In one embodiment, the method according to the invention does not comprise adjusting the pH of the filtered protein solution at the end of the filtration step and/or of the retentate at the end of the exchanging step.

In a particular embodiment, the filtered protein solution obtained at the end of the filtration step is directly passed over the diafiltration membrane. More specifically, no treatment (such as pH adjustment, buffer exchange or dilution) is then carried out between the two steps. In such a method, the diafiltration membrane may for example correspond to a Ready To Process 30 kD hollow fiber module or a Cadence Inline Diafiltration module, preceded or followed for example by a Cadence Inline Concentrator. Additionally, in a particular embodiment, the retentate obtained at the end of the exchanging step is directly passed through the combination of membrane adsorbers of the polishing step. More specifically, no treatment (such as pH adjustment, buffer exchange or dilution) is then carried out between the two steps. In such a method, the diafiltration membrane may for example correspond to a Ready To Process 30 kD hollow fiber module and/or the combination of membrane adsorbers may for instance correspond to a combination of Sartobind S membrane adsorber and of Sartobind STIC membrane adsorber.

In such a method, inter-step treatments requiring manual intervention and opening of the purification system (e.g., dilution, conductivity adjustment and pH adjustment) are totally absent.

The method of the invention may thus be performed in a flexible automated chromatographic system comprising multiples pumps and sensors with interconnection and switching valves for operation in sequence or in continuous of the 3 purification steps.

A non-limiting example of a multi-operation system is a multi-column chromatography system MCCS with appropriate adaptation.

The method of the invention can be run in continuous mode. In other words, the method of the invention can be a continuous method for purifying a protein from solution.

The term "continuous method" or "method in a continuous mode" means a method which continuously feeds fluid through at least a part of the system.

By the term "fluid", it is meant herein any liquid, such as a solution containing the protein to be purified, a buffer or a low or acidic pH solution for viral inactivation.

In a particular embodiment, the first, second and third purification steps are continuously fed through with a fluid.

The term "integrated process" means a process which is performed using structural elements that function cooperatively to achieve a specific result (e.g. the generation of a purified protein from a liquid culture medium).

Furthermore, the method of the invention can be run in a closed system from the first step of the method to the last one. In other words, the method of the invention preferably has a flowpath functionally closed. In particular, the three purification steps and the optional filtration step(s) (for example, the nanofiltration step and/or the final ultrafiltration and/or diafiltration step) can be run in a closed system. In a specific embodiment of the method of the invention, the solution comprising proteins is passed, parts by parts, over the three purification steps, each passage of a part of the solution corresponding to a run. The proteins recovered at the end of each run are then collected and pooled. In such a method, the membrane adsorber of a purification step is used several times, and optionally sanitated using for example a sanitization buffer as defined above, thereby enabling reducing the volume of membrane adsorber devices, and buffer needed. For instance, a sequence of 3 to 50 runs (e.g. 3 to 30 runs, 5 to 25 runs, 10 to 20 runs, or 15 runs) can be performed continuously. More specifically, 3, 4, 5, 6, 7 or 8 runs can be performed in continuous mode, followed by sanitization of the membrane adsorbers (e.g. using the sanitization buffer). This might be repeated e.g. 2, 3, 4, 5, 6, 7, 8, 9, 10 or more times as illustrated on FIG. 2.

The method disclosed herein can be used to recover purified proteins. As used herein, "purified" refers to a purity that allows for the effective use of the protein in vitro, ex vivo, or in vivo. For a protein to be useful in in vitro, ex vivo, or in vivo applications, it should be substantially free of contaminants, other proteins, and/or chemicals that could interfere with the use of that protein in such applications, or that at least would be undesirable for inclusion with the protein of interest. Such applications include that preparation of therapeutic compositions, the administration of the protein in a therapeutic composition, and other methods disclosed herein. Preferably, a "purified" protein, as referenced herein, is a protein that can be produced by any method (i.e., by direct purification from a natural source, recombinantly, or synthetically), and that has been purified from other protein components such that the protein comprises at least about 70% weight/weight of the total protein in a given composition, and more preferably, at least about 80% or at least about 85%, and more preferably at least about 90%, and more preferably at least about 91%, and more preferably at least about 92%, and more preferably at least about 93%, and more preferably at least about 94%, and more preferably at least about 95%, and more preferably at least about 96%, and more preferably at least about 97%, and more preferably at least about 98%, and more preferably at least about 99% weight/weight of the total protein in a given composition.

In a particular embodiment, the method of the invention comprises:

(a) a filtration step comprising:
   (i) passing the solution over the at least one chelating agent matrix in the flow-through mode,
   (ii) recovering a filtered protein solution from the flow-through of said at least one chelating agent matrix,
(b) an exchanging step comprising:
   (i) passing the filtered protein solution obtained from step (a) and the one buffer over the at least one diafiltration membrane,
   (ii) recovering the partly purified protein-containing retentate of said at least one diafiltration membrane;

and (c) a polishing step comprising:
   (i) passing equilibration buffer over the combination of membrane adsorbers, wherein said equilibration buffer is identical to the one buffer used for exchange at step (b),
   (ii) passing the retentate obtained from step (b) over the combination of membrane adsorbers in the flow-through mode,
   (iii) recovering purified protein from the flow-through of said combination of membrane adsorbers, wherein said purifying method does not include a Protein A chromatography step, wherein the one buffer comprises or consists of:

- 5 to 40 mM (e.g. 20 mM) Bis Tris and 15 to 150 mM (e.g. 75 mM) NaCl, adjusted to a pH comprised between 6 and 9 (e.g. 7.5) with acetic acid,
- 5 to 40 mM (e.g. 20 mM) Tris or Tris-HCl, 15 to 150 mM (e.g. 75 mM) NaCl, adjusted to a pH comprised between 6 and 9 (e.g. 7.5) with acetic acid,
- 5 to 40 mM (e.g. 20 mM) Tris or Tris-HCl, 15 to 150 mM (e.g. 75 mM) NaCl, adjusted to a pH comprised between 6 and 9 (e.g. 7.5) with citric acid, or
- 15 to 150 mM (e.g. 75 mM) NaCl, adjusted to a pH comprised between 6 and 9 (e.g. 7.5) with $Na_2HPO_4$/$NaH_2PO_4$ (preferably from 10 mM/90 mM $Na_2HPO_4$/$NaH_2PO_4$ to 90 mM/10 mM $Na_2HPO_4$/$NaH_2PO_4$).

The method for purifying a protein from solution may comprise at least an additional final filtration step, after the polishing step, such as a nanofiltration step, an ultrafiltration step and/or a diafiltration step. When purifying recombinant proteins for pharmaceutical purposes, the polishing step typically followed by additional final filtration steps. Therefore, the method of the invention may further comprise a nanofiltration step after step (c). An ultrafiltration and diafiltration step may further be carried out after the nanofiltration step. As used herein, "ultrafiltration" or "UF" refers to a filtration technique using a semi-permeable membrane to physically and selectively remove particles and/or ions from a solution based on particle size and size of the pores in the UF membrane. As used herein, "nanofiltration" refers to filtration of a solution through a nanofilter that is used to remove, e.g., viral particles. As used herein, "diafiltration" refers a technique that uses ultrafiltration membranes to completely remove, replace, or lower the concentration of salts or solvents from solutions.

The method of the invention may also further comprise at least one viral inactivation step. Said at least one viral inactivation step may be performed at any stage of the method of the invention, for example before step (a), after step (a), after step (b), after step (c), after the nanofiltration step and/or after the ultrafiltration and/or diafiltration step. Such a viral inactivation step may typically be a low or acidic pH inactivation step. As used herein, "low or acidic pH inactivation" refers to a viral inactivation technique using acidic pH to denature viruses, in particular enveloped viruses. Typically, the low or acidic pH inactivation step is carried out by incubating the recovered proteins at a pH of between about 3.0 to 5.0 (e.g., between about 3.5 to about 4.5, between about 3.5 to about 4.25, between about 3.5 to about 4.0, for example 4.0) for a period of at least 15 minutes (e.g., a period of between 15 minutes to 1 hour, a period of between about 30 minutes to 2 hours, or a period of between about 45 minutes to 2 hours). For example, the low or acidic pH inactivation step is carried out by incubating the recovered proteins at a pH of 4 during for example 30 minutes to 2 hours.

The method of the invention may also comprise, before step (a), a step of providing a liquid culture medium containing the protein to be purified that has been clarified to remove cells and is substantially free of cells, wherein said liquid culture medium is fed over the at least one chelating agent matrix.

For example, the method of the invention for purifying a protein from solution may comprise:

(pre-a) a step of providing a liquid culture medium containing the protein to be purified that has been clarified to remove cells and is substantially free of cells,
(a) a filtration step comprising:
   passing said liquid culture medium of step (pre-a) over at least one chelating agent matrix in the flow-through mode;
   recovering a filtered protein solution from the flow-through of said at least one chelating agent matrix;
(b) an exchanging step comprising:
   passing the filtered protein solution obtained at the end of step (a) over at least one diafiltration membrane using only one buffer for the exchange;
   recovering the partly purified protein-containing retentate of said at least one diafiltration membrane; and
(c) a polishing step comprising:
   passing the retentate obtained at the end of step (b) over a combination of membrane adsorbers in the flow-through mode, wherein two membrane adsorbers of said combination of membrane adsorbers are orthogonal in terms of mechanism of action, and said combination of membrane adsorbers has been equilibrated beforehand with an equilibration buffer which is identical to the one buffer used for exchange at step (b);
   recovering purified protein from the flow-through of said combination of membrane adsorbers;

wherein said purifying method does not include a Protein A chromatography step.

Finally, the purified protein may be formulated into a composition suitable for storage, and/or into a pharmaceutical composition, in particular suitable for administration to animals and/or humans.

One of the numerous advantages of the disclosed method is that it allows obtaining good yields of highly pure protein. The purified protein that is recovered with the method of the invention can for instance exhibit a purity of at least 70%, 75%, 80%, 85%, 90%, 95%, 96%, 97%, 98%, 99%, 99.2%, 99.5%, or 99.9%. More particularly, one of the numerous advantages of the disclosed method is that it allows obtaining solutions of highly pure protein containing reduced amounts of contaminating DNA, of high molecular weight (HMW) species (which correspond to protein aggregates) and/or of host cell proteins (HCP). The solution comprising purified protein that is recovered with the method of the invention can for instance exhibit an amount of contaminating DNA of less than 0.4 ppb, less than 0.3 ppb, less than 0.2 ppb or less than 0.1 ppb. The solution comprising purified protein that is recovered with the method of the invention can also for instance exhibit a concentration of HMW species of less than 0.6%, less than 0.5%, less than 0.4%, less than 0.3%, less than 0.2% or less than 0.1%. The solution comprising purified protein that is recovered with the method of the invention can also for instance exhibit a concentration of HCP of less than 500 ng/ml, less than 100 ng/ml, less than 90 ng/ml, less than 85 ng/ml, less than 80 ng/ml, less than 75 ng/ml or less than 70 ng/ml. In addition, the method of the invention can allow recovering the purified protein with a yield of at least 70%, 75%, 80%, 85%, 90%, 95%, 96%, 97%, 98% or 99%.

The invention further pertains to a kit comprising or consisting of:

(a) at least one chelating agent matrix, at least one diafiltration membrane and a combination of membrane adsorbers, wherein two membrane adsorbers of said combination of membrane adsorbers are orthogonal in terms of mechanisms of action; and (b) one buffer comprising Tris, Tris-HCl, Bis Tris, phosphate and/or citric acid, in particular comprising or consisting of (i) Bis Tris, Tris, or Tris-HCl, (ii) acetic acid, (iii) water, and (iv) optionally NaCl; and/or instructions for preparing one buffer comprising Tris, Tris-HCl, Bis Tris, phosphate and/or citric acid, in particular comprising or consisting of (i) Bis Tris, Tris or Tris-HCl, (ii) acetic acid, (iii) water, and (iv) optionally NaCl.

The present invention will be further illustrated by the figures and examples below.

EXAMPLES

Figure 1:
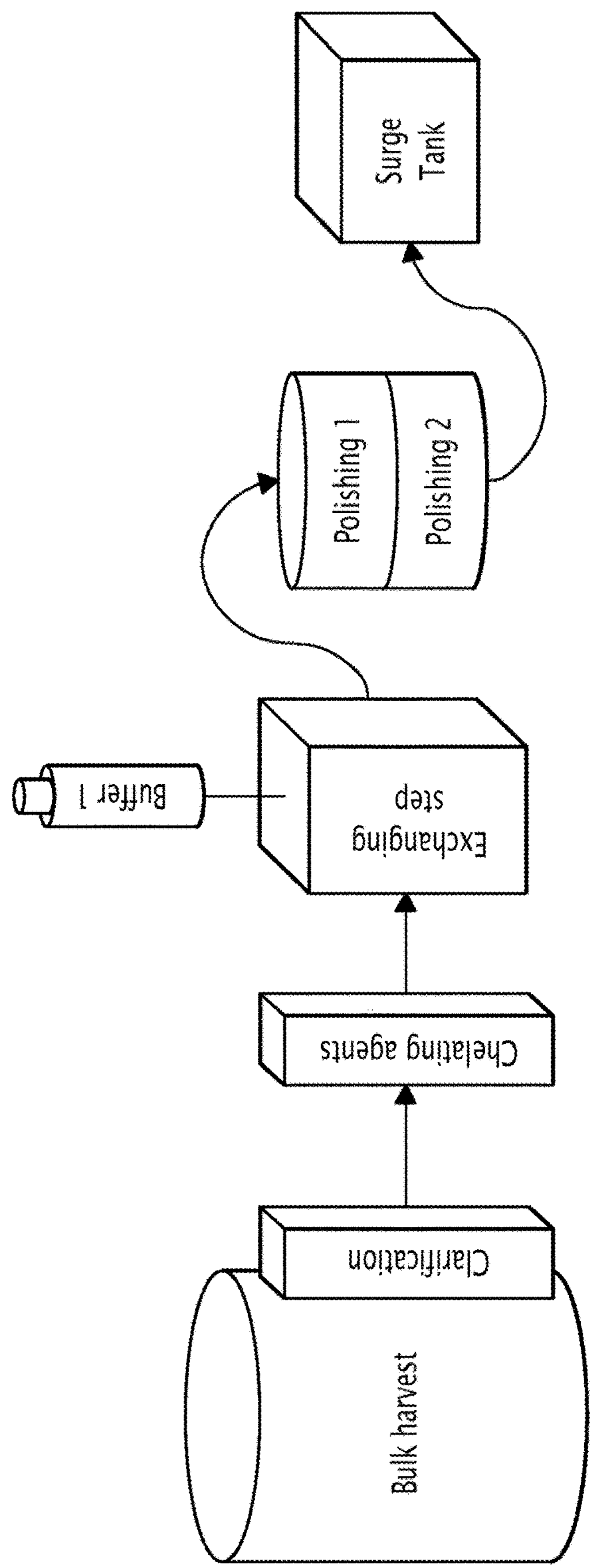
FIG. 1 shows a scheme representing the 3-steps full flow-through method of the invention.
Figure 2:
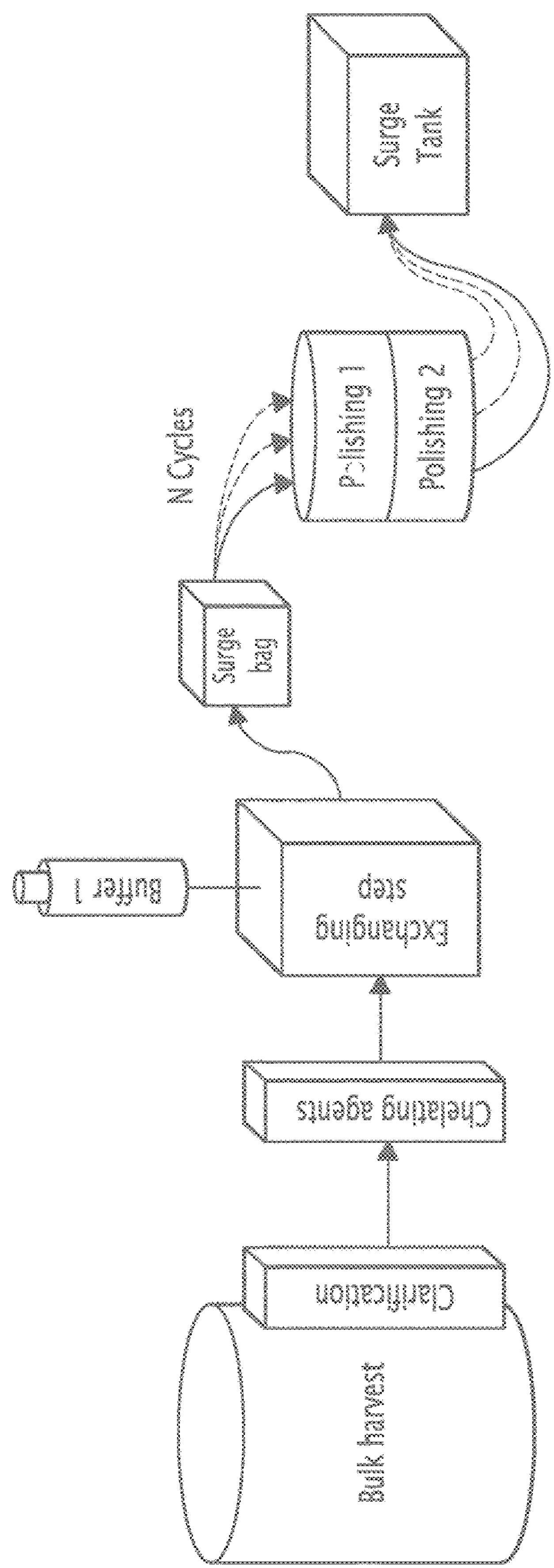
FIG. 2 shows a scheme representing a continuous version of the 3-steps full flow-through method of the invention as used in Example 4.
Figure 3:
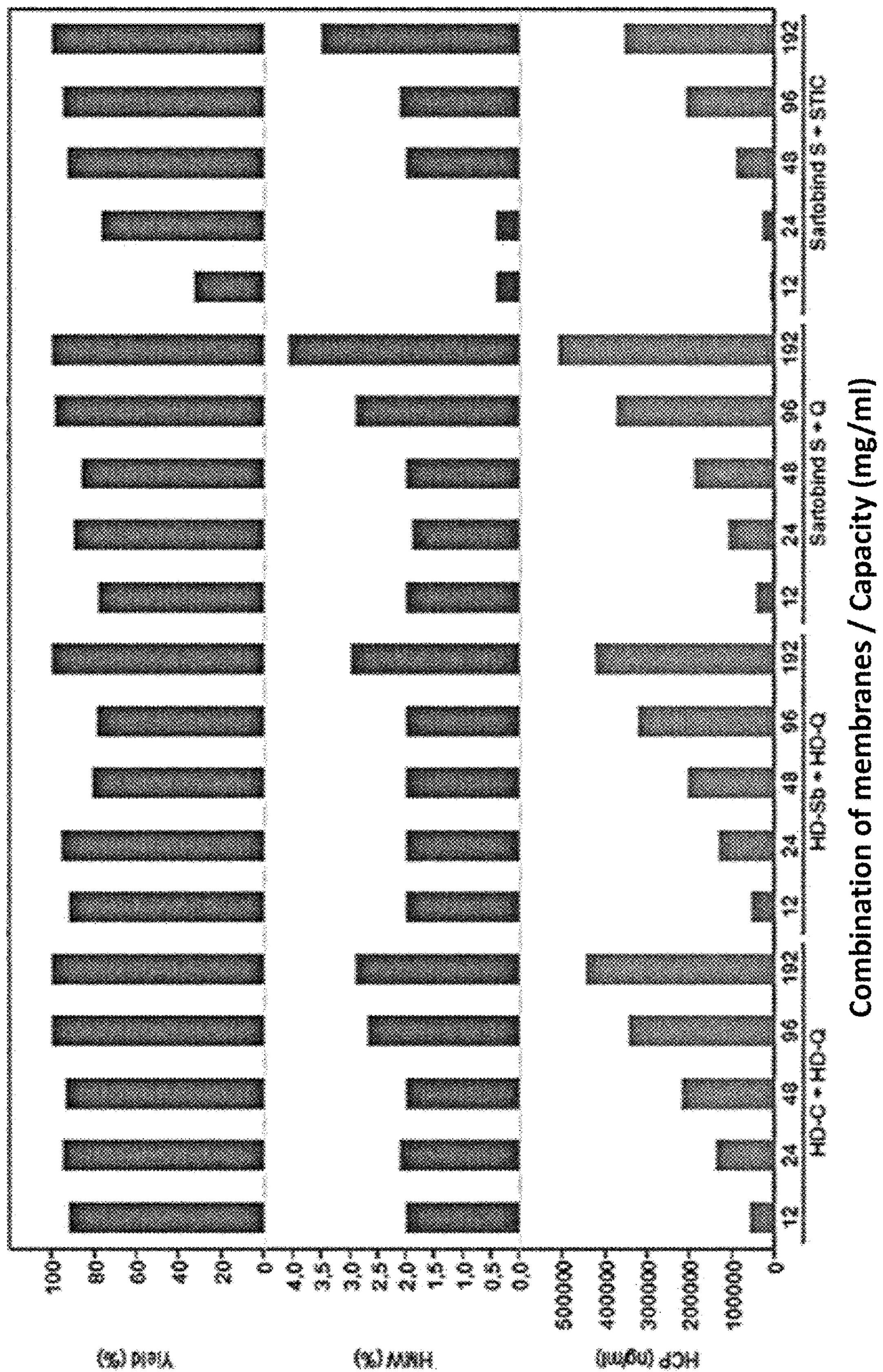
FIG. 3 shows histograms representing the comparison of the yield (%), HMW (%) and HCP (ng/ml) obtained with 4 combinations of membrane adsorbers (HD-C+HD-Q; HD-Sb+HD-Q; Sartobind S+Q; Sartobind S+STIC) according to the capacity (mg/ml) of the membranes.
Figure 4:
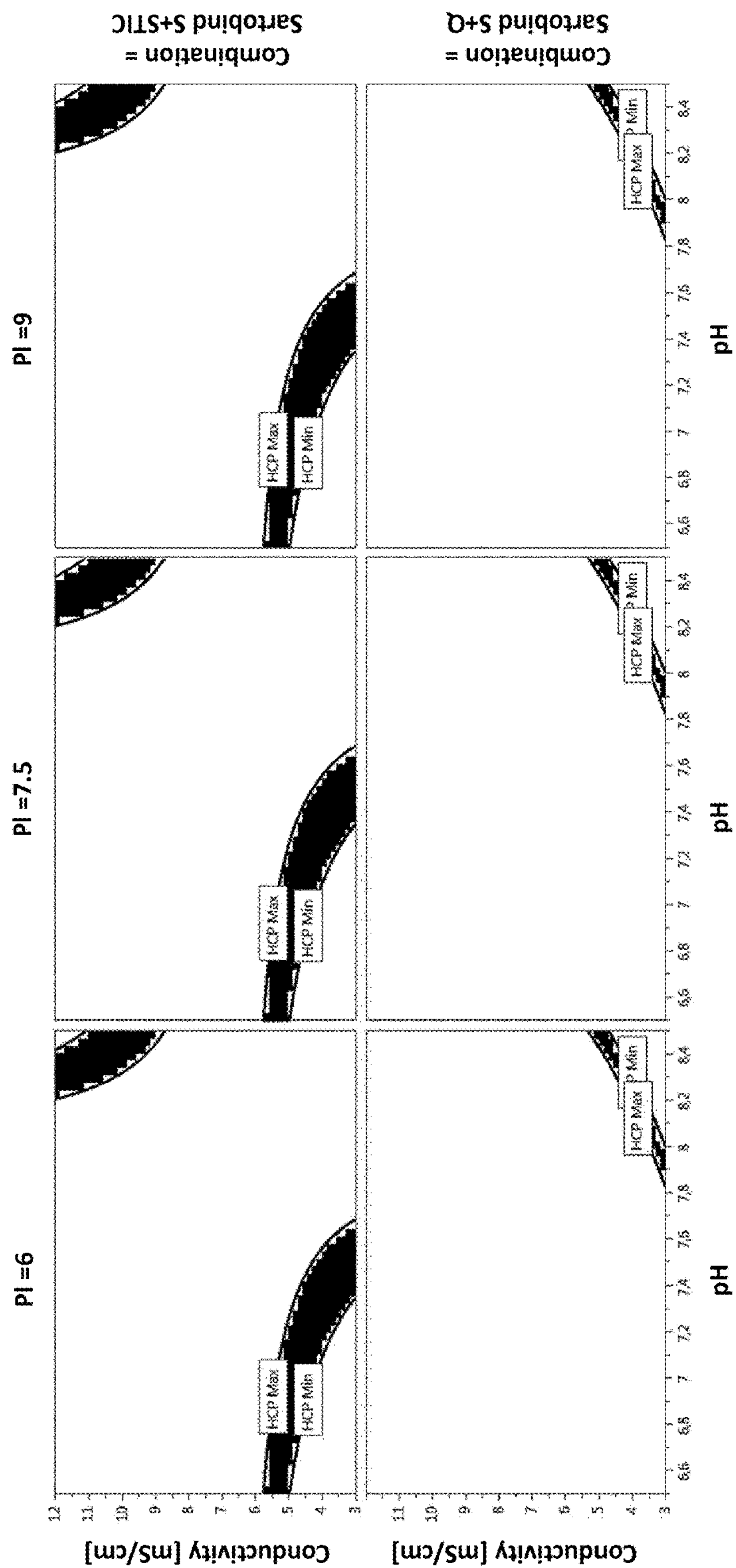
FIG. 4 shows a Sweet Spot plot for two combinations of membrane adsorbers (upper panel: Sartobind S+STIC; lower panel: Sartobind S+Q) and 3 pI of the protein to be purified (6; 7.5 and 9) according to the pH and the conductivity (mS/cm) of the equilibration buffer. The conditions of pH and conductivity enabling obtaining an advantageous purification (corresponding to an HCP level comprising between 50 and 500 ng/ml) correspond to the black areas of each plot.

Example 1: Lab-Scale Process According to the Invention

The method of the invention was utilized for lab-scale batch purification of a humanized monoclonal antibody mAb1.

This experiment show the results of impurities removal obtained at labscale after the three steps. The goal was to remove aggregates (HMW) and host cells protein (HCP) below 1% for HMW and 500 ng/ml for HCP.

The inventors succeeded using 2 different chelating agents, one exchanging step and a couple of membranes (Sartobind S and STIC or Sartobind S and Q).

| | Step | Conditions (pH/ conductivity) | HMW (%) | HCP (ng/ml) |
|---|---|---|---|---|
| Filtration step | Bulk harvest | Starting material | 5.6 | 822 039 |
| | $NH_2$-750F resin | Added in the bulk and stirred | 2.0 | 519 516 |
| | Activated carbon CA1 | Added in the bulk and stirred | 1.9 | 179 002 |
| | Activated carbon CA2 | Added in the bulk and stirred | 2.0 | 143 765 |
| Exchanging step | UF/DF 30 kD concentration | | 2.2 | 474 742 |
| | UF/DF 30 kD diafiltration | | 2.7 | 488 279 |
| | Filtration 0.2 μm | | — | — |
| Polishing step | Sartobind S + Q membranes | pH 8.5 - 3 mS/cm | 0 | 1582 |
| | Sartobind S + STIC membranes | pH 8.5 - 3 mS/cm | 0 | 348 |
| | Sartobind S + Q membranes | pH 7.5 - 3 mS/cm | 0 | 2023 |
| | Sartobind S + STIC membranes | pH 7.5 - 3 mS/cm | 0 | 604 |
| | Sartobind S + Q membranes | pH 6.5 - 3 mS/cm | 0 | 7968 |
| | Sartobind S + STIC membranes | pH 6.5 - 3 mS/cm | 0 | 656 |
| | Sartobind S + Q membranes | pH 8.5 - 12 mS/cm | 0.8 | 11591 |
| | Sartobind S + STIC membranes | pH 8.5 - 12 mS/cm | 0 | 3297 |
| | Sartobind S + Q membranes | pH 7.5 - 12 mS/cm | 2.4 | 34727 |
| | Sartobind S + STIC membranes | pH 7.5 - 12 mS/cm | 0 | 3639 |
| | Sartobind S + Q membranes | pH 6.5 - 12 mS/cm | 3.0 | 63484 |
| | Sartobind S + STIC membranes | pH 6.5 - 12 mS/cm | 0 | 5589 |

Example 2: Lab-Scale Process According to the Invention

The method of the invention was utilized for lab-scale batch purification of a humanized monoclonal antibody mAb2.

This experiment shows the results of impurities removal obtained at labscale after the three steps. The goal was to remove aggregates (HMW) and host cells proteins (HCP) below 1% for HMW and 500 ng/ml for HCP. The inventors succeeded using 2 kinds of chelating agents, one exchanging step and a couple of membranes (Sartobind S and STIC or Sartobind S and Q). The best result is obtained with the couple Sartobind S+STIC, with a loading conditions set at pH 8.5 and 3 ms/cm.

| | Step | Conditions (pH/ conductivity) | HMW (%) | HCP (ng/ml) |
|---|---|---|---|---|
| Filtration step | Bulk harvest | Starting material | 8.8 | 644 359 |
| | $NH_2$-750F resin | Added in the bulk and stirred | 2.0 | 320 476 |
| | Activated carbon CA1 | Added in the bulk and stirred | 1.6 | 73 281 |
| | Activated carbon CA2 | Added in the bulk and stirred | 0.5 | 43 153 |
| Exchanging step | UF/DF 50 kD concentration | | | |
| | UF/DF 50 kD diafiltration | | | |
| | Filtration 0.2 μm | | 0.7 | 333 573 |
| Polishing step | Sartobind S + Q membranes | pH 8.5 - 3 mS/cm | 0.1 | 882 |
| | Sartobind S + STIC membranes | pH 8.5 - 3 mS/cm | 0.2 | 182 |
| | Sartobind S + Q membranes | pH 7.5 - 3 mS/cm | 0.1 | 743 |
| | Sartobind S + STIC membranes | pH 7.5 - 3 mS/cm | 0.0 | 262 |
| | Sartobind S + Q membranes | pH 6.5 - 3 mS/cm | 0.0 | 5522 |
| | Sartobind S + STIC membranes | pH 6.5 - 3 mS/cm | 0.0 | 1117 |
| | Sartobind S + Q membranes | pH 8.5 - 12 mS/cm | 0.6 | 11 001 |
| | Sartobind S + STIC membranes | pH 8.5 - 12 mS/cm | 0.0 | 2710 |
| | Sartobind S + Q membranes | pH 7.5 - 12 mS/cm | 0.6 | 12 961 |
| | Sartobind S + STIC membranes | pH 7.5 - 12 mS/cm | 0.1 | 6463 |
| | Sartobind S + Q membranes | pH 6.5 - 12 mS/cm | 0.6 | 63553 |
| | Sartobind S + STIC membranes | pH 6.5 - 12 mS/cm | 0.2 | — |

Example 3: Pilot-Scale Process According to the Invention

The method of the invention was utilized for pilot-scale batch purification of mAb1.

The same process as the one disclosed in Example 2 was scaled-up at pilot scale. The aim was to purify 10 g through the three steps followed by nanofiltration step.

8 L of clarified cell culture supernatant were purified through the three steps of the method of the invention and a nanofiltration. The 8 L were introduced in a 20 L mixer with successively: 250 ml of Tosoh NH2-750F resin, then stirred 13 min, 160 g of Activated Carbon (Norit SA2 grade), then stirred 14 min and 30 g of Activated Carbon (Norit SA2 grade), then stirred 10 min.

The product was filtered (Filtrox filter) before starting the exchanging step. Around 9 L of product was recovered after the filtration (product pushed outside of filter with 1 L of sterile water). UF/DF was performed using an Hollow fiber (790 $cm^2$-50 KD—Spectrumlabs) on a GE Uniflux. The buffer used to diafiltrate the product through the hollow fiber was a 20 mM Bis Tris Q.S. to acetic acid pH 7.2 buffer.

2.64 kg were recovered at 6.9 g/L (18.2 g of monoclonal antibody). Then 2 L (14 g) of recovered product was pushed through two membranes adsorbers: 75 ml Sartobind S 200 ml Sartobind Q. The two membranes were linked in serial and use in flowthough mode using an GE AktaProcess.

Finally the product was nanofiltered though a prefilter (XOHC—Millipore) and a Viresolve Pro filter (Millipore) to obtain the final quality.

The table below shows the comparison between a conventional process and the method of the invention.

| | Conventional process | Process of the invention |
|---|---|---|
| | Process comparison | |
| Steps | Protein A + mixed mode + AEX resins | Chelating agents + Exchanging step + polishing step |
| Number of columns | 3 | 0 |
| Number of buffers | 7 (excluding sanitization buffers) | 1 (excluding sanitization buffers) |
| Duration | 13 h | 8 h 30 |
| Yield | 80% | 70% |
| | Final quality | |
| HMW (%) | 0.4 | 0.1 |
| HCP (ng/ml) | 100 | 70 |
| DNA (ppm) | <1 | <1 |

Example 4: Full Continuous Lab-Scale Process According to the Invention

The method of the invention was utilized for lab-scale batch purification of humanized monoclonal antibody mAb1 in continuous mode.

The aim of the experiment was to purify mAb1 from Clarified Bulk Harvest using continuous mode meaning no interruption, storage or adjustment between each step. The inventors succeeded using a filtration on chelating agent (Immobilized AEX, Activated Carbon CA), one exchanging step (Single Pass Diafiltation) and a couple of membranes (Sartobind S and STIC).

3 L of clarified cell culture supernatant were purified through the three steps of the method of invention. The product was filtered through an immobilized anion exchanger (Emphaze AEX BV120) and then an activated Carbon Filter (Millipore CR40 270 cm2). The product then flowed directly into a single pass diafiltration membrane (0.2 m2) for concentration and diafiltration (exchanging step). The buffer used to diafiltrate the product through was a 20 mM Bis Tris, 20 mM NaCl Q.S. to acetic acid pH 7.5 buffer.

The diafiltered product directly recovered from the retentate side passed through an intermediate surge bag to accommodate the flow differences with the following step. The product was then further pushed through the two polishing membranes adsorbers; 1 ml Sartobind S and 1 ml Sartobind STIC. The two membranes were linked in serial and used in flowthrough mode using a GE Akta Pure. Each unit step is directly connected to the other or through a surge bag and processed continuously.

Figure 5:
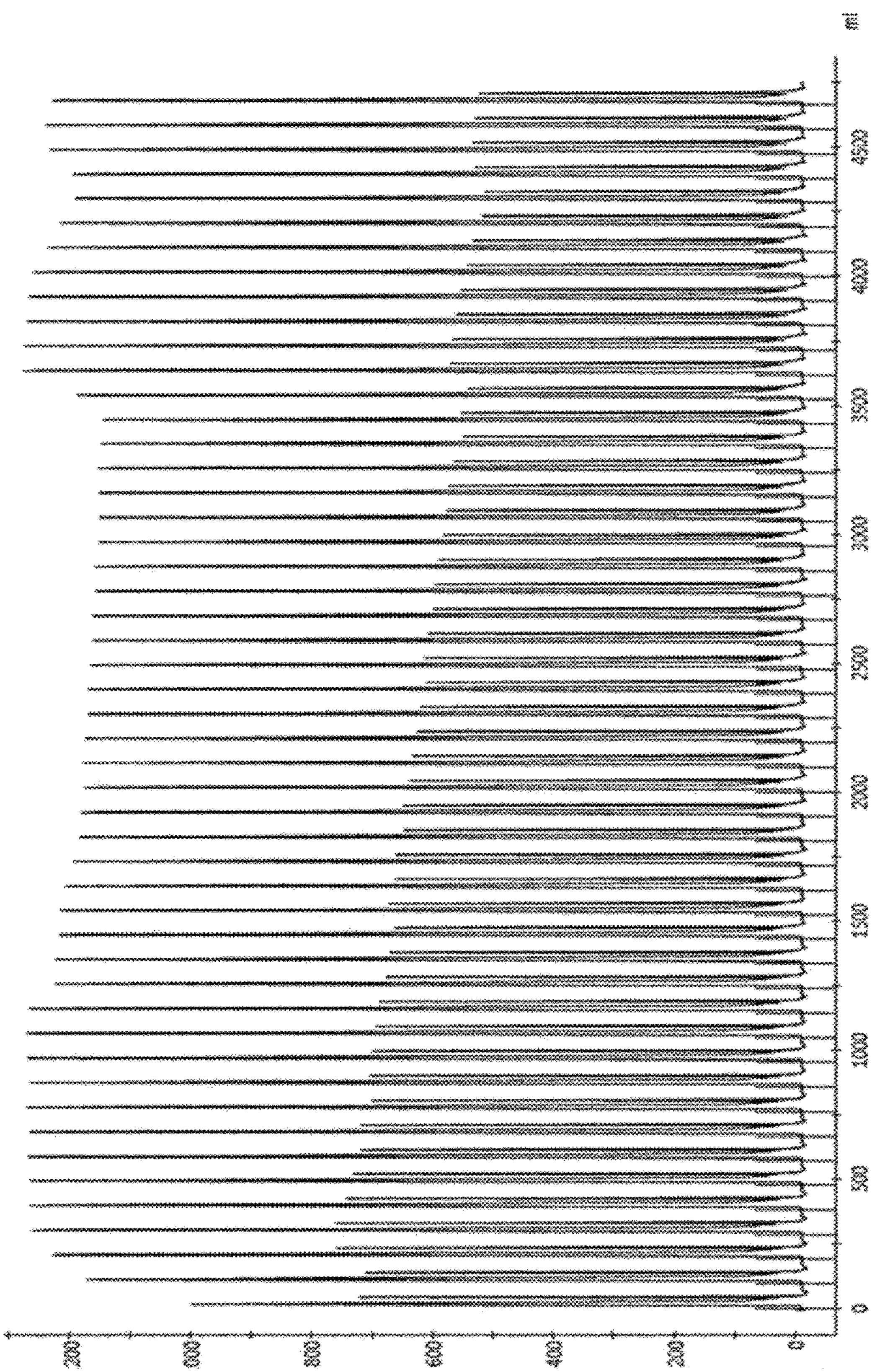
FIG. 5 shows a partial chromatogram of the purification (U.V. 280 nm) over the membrane during the continuous lab-scale process experiment.

Multiples cycles of purification were performed on the membranes adsorbers to process the entire volume of product, as shown on FIG. 5 (extract of 50 cycles of purification on the membranes). The entire product pool was recovered through a sterile filter at the end of the process. 40 mg of mAb were purified every 5 minutes leading to a productivity of 240 g of mAb1 per liter of membrane per hour (240 g/L/h).

The invention claimed is:

1. A full flow-through method for purifying a protein from solution comprising:

(a) a filtration step comprising:

passing said solution over at least one chelating agent matrix in the flow-through mode, wherein said at least one chelating agent matrix is activated carbons, recovering a filtered protein solution from the flow-through of said at least one chelating agent matrix;

(b) an exchanging step comprising:

passing the filtered protein solution obtained at the end of step (a) over at least one diafiltration membrane using only one buffer for the exchange, recovering the partly purified protein-containing retentate of said at least one diafiltration membrane; and (c) a polishing step comprising:

passing the retentate obtained at the end of step (b) over a combination of membrane adsorbers in the flow-through mode, wherein two membrane adsorbers of said combination of membrane adsorbers are orthogonal in terms of mechanisms of action, and said combination of membrane adsorbers has been equilibrated beforehand with an equilibration buffer which is identical to the one buffer used for exchange at step (b), recovering purified protein from the flow-through of said combination of membrane adsorbers;

wherein said purifying method does not include a Protein A chromatography step.

2. The method of claim 1, wherein the filtered protein solution obtained at the end of step (a) is directly passed over the at least one diafiltration membrane, without undergoing any treatment such as pH adjustment, buffer exchange or dilution.

3. The method of claim 1, wherein the retentate obtained at the end of step (b) is directly passed over said combination of membrane adsorbers, without undergoing any treatment such as pH adjustment, buffer exchange or dilution.

4. The method of claim 1, wherein the method does not comprise any intermediate storage between the three steps (a), (b) and (c).

5. The method of claim 1, wherein the method has a flowpath functionally closed.

6. The method of claim 1, wherein only one buffer is used over the whole purification method.

7. The method of claim 1, wherein the one buffer comprises Tris, Tris-HCl, Bis Tris, phosphate and/or citric acid, in particular comprises or consists of (i) Bis Tris, Tris or Tris-HCl, (ii) acetic acid, (iii) water and (iv) optionally salt.

8. The method of claim 1, wherein the at least one chelating agent matrix of the filtration step is a combination of two or more than two different chelating agent matrices and said second chelating agent matrix is selected from the group consisting of diatomite earth, free cationic exchange resin, free anionic exchange resin, and free mixed mode resin.

9. The method of claim 8, wherein the at least one chelating agent matrix is a combination of two different chelating agent matrices.

10. The method of claim 9, wherein the combination of two different chelating agent matrices is a combination of activated carbons and free anionic exchange resin.

11. The method of claim 1, wherein the at least one diafiltration membrane of the exchanging step is a single-path tangential flow filtration (SPTFF) module or a tangential flow filtration (TFF) module.

12. The method of claim 1, wherein the at least one diafiltration membrane of the exchanging step is in the form of a cassette, a hollow fiber or a spiral wound.

13. The method of claim 1, wherein the filtered protein solution is concentrated during the exchanging step.

14. The method of claim 1, wherein the combination of membrane adsorbers of the polishing step is a combination of at least two membrane adsorbers selected from the group consisting of cationic-exchange membrane adsorbers, anionic-exchange membrane adsorbers, multi-modal membrane adsorbers and hydrophobic interaction membrane adsorbers.

15. The method of claim 1, wherein the combination of membrane adsorbers of the polishing step is a combination of a cationic-exchange membrane adsorber and an anionic-exchange membrane adsorber.

16. The method of claim 1, further comprising a nanofiltration step after step (c).

17. The method of claim 16, further comprising a final ultrafiltration and/or diafiltration step after the nanofiltration step.

18. The method of claim 1, wherein the protein is a monoclonal antibody.

19. The method of claim 1, wherein the one buffer comprises:

5 to 40 mM Bis Tris, 15 to 150 mM NaCl, adjusted to a pH comprised between 6 and 9 with acetic acid, 5 to 40 mM Tris or Tris-HCl, 15 to 150 mM NaCl, adjusted to a pH comprised between 6 and 9 with acetic acid, 5 to 40 mM Tris or Tris-HCl, 15 to 150 mM NaCl, adjusted to a pH comprised between 6 and 9 with citric acid, or 15 to 150 mM NaCl, adjusted to a pH comprised between 6 and 9 with $Na_2HPO_4/NaH_2PO_4$.

20. The method of claim 1, further comprising the step of formulating the recovered purified protein into a pharmaceutical composition.

* * * * *